(12) United States Patent
Beaubien (10) Patent No.: US 10,898,702 B2
(45) Date of Patent: Jan. 26, 2021

(54) DEVICES AND METHODS FOR APPLYING BODY LOTIONS SUCH AS SUNSCREENS

(71) Applicant: Barry Beaubien, Howell, MI (US)

(72) Inventor: Barry Beaubien, Howell, MI (US)

(73) Assignee: Barry Beaubien, Howell, MI (US)

( * ) Notice: Subject to any disclaimer, the term of this patent is extended or adjusted under 35 U.S.C. 154(b) by 0 days.

(21) Appl. No.: 16/364,942

(22) Filed: Mar. 26, 2019

(65) Prior Publication Data

US 2019/0218019 A1 Jul. 18, 2019

Related U.S. Application Data

(63) Continuation-in-part of application No. 15/662,938, filed on Jul. 28, 2017, now abandoned, which is a continuation of application No. 14/475,939, filed on Sep. 3, 2014, now Pat. No. 9,725,229.

(60) Provisional application No. 61/873,050, filed on Sep. 3, 2013.

(51) Int. Cl.
| | |
|---|---|
| *A61M 35/00* | (2006.01) |
| *A45D 34/04* | (2006.01) |
| *A45D 40/26* | (2006.01) |
| *B05C 17/02* | (2006.01) |
| *B05C 17/03* | (2006.01) |

(52) U.S. Cl.
CPC .......... *A61M 35/003* (2013.01); *A61M 35/00* (2013.01); *A45D 34/04* (2013.01); *A45D 40/261* (2013.01); *A45D 2200/1081* (2013.01); *B05C 17/02* (2013.01); *B05C 17/022* (2013.01); *B05C 17/0217* (2013.01); *B05C 17/0333* (2013.01); *B05C 17/0341* (2013.01)

(58) Field of Classification Search
CPC . B65D 83/0894; A61M 35/00; A61M 35/003; A45D 34/00; A45D 2200/1081; A45D 34/04; A45D 34/041; A45D 40/26; A45D 40/261; B05C 17/02; B05C 17/0205; B05C 17/0207; B05C 17/0217; B05C 17/022; B05C 17/0333; B05C 17/0341
See application file for complete search history.

(56) References Cited

U.S. PATENT DOCUMENTS

| | | | | |
|---|---|---|---|---|
| 1,075,941 | A | * | 10/1913 | Reed ................. B05C 17/035 401/219 |
| 2,722,029 | A | * | 11/1955 | Barnes ............... B05C 17/0308 401/197 |
| 3,036,328 | A | * | 5/1962 | Schaich .............. A45D 34/041 401/213 |
| 4,150,904 | A | | 4/1979 | Stewart |
| 4,225,254 | A | | 9/1980 | Holberg et al. |
| 4,759,652 | A | | 7/1988 | Ulrich |
| D333,191 | S | | 2/1993 | Rainen |
| 5,660,636 | A | | 8/1997 | Shangold et al. |
| | | | (Continued) | |

FOREIGN PATENT DOCUMENTS

| | | |
|---|---|---|
| EP | 0891725 A1 | 1/1999 |
| EP | 2206447 A1 | 7/2010 |

*Primary Examiner* — David J Walczak
(74) *Attorney, Agent, or Firm* — Dinsmore & Shohl LLP (57) ABSTRACT

Hand-held articles for applying lotion to a user, including a user's back or other hard-to-reach places have a housing containing a lotion to be dispensed, and a roller, integral to the housing, that transfers the lotion to a user's body. A spring or pump mechanism pushes the lotion in the housing towards the roller.

16 Claims, 7 Drawing Sheets

(56) References Cited

U.S. PATENT DOCUMENTS

| | | | |
|---|---|---|---|
| 5,851,077 A | 12/1998 | Trejo | |
| 5,871,297 A | 2/1999 | Rogers et al. | |
| 6,017,162 A | 1/2000 | Call | |
| 6,244,776 B1 | 6/2001 | Wiley | |
| 6,382,552 B1 | 5/2002 | Paul et al. | |
| 6,412,997 B2 * | 7/2002 | Berke | A45D 34/04 401/138 |
| 6,530,707 B1 | 3/2003 | Byrne et al. | |
| 6,543,954 B2 | 4/2003 | Owings | |
| 6,607,514 B2 | 8/2003 | Reese | |
| 7,044,670 B2 | 5/2006 | Delage | |
| 7,101,106 B1 | 9/2006 | Wiley | |
| D663,479 S | 7/2012 | Ammerman | |
| 8,757,914 B1 * | 6/2014 | Megaro | A45D 34/041 401/219 |
| 2010/0303532 A1 * | 12/2010 | Brunozzi | A45D 34/00 401/6 |
| 2012/0282199 A1 | 11/2012 | Pollack et al. | |
| 2014/0153996 A1 * | 6/2014 | Ammerman | A45D 34/041 401/219 |

\* cited by examiner

DEVICES AND METHODS FOR APPLYING BODY LOTIONS SUCH AS SUNSCREENS

REFERENCE TO RELATED APPLICATIONS

This application is a continuation-in-part of U.S. patent application Ser. No. 15/662,938, filed on Jul. 28, 2017, which is a continuation of U.S. patent application Ser. No. 14/475,939, filed Sep. 3, 2014, now U.S. Pat. No. 9,725,229, which claims priority from U.S. Provisional Patent Application Ser. No. 61/873,050, filed Sep. 3, 2013, the entire content of each of which is incorporated herein by reference.

FIELD OF THE INVENTION

This invention relates generally to lotion dispensers and, in particular, to devices and methods for applying lotions such as sunscreens.

BACKGROUND OF THE INVENTION

There are many occasions wherein an individual desires to apply a body lotion prior to a trip to the beach or a session at a tanning salon, but the applicator choices are limited. At a tanning salon, it would be advantageous to provide one-time, disposable, or rechargeable applicators so that a user need not purchase or bring a large bottle of lotion. Further, whether at the salon or the beach, it would be advantageous if the device and method enabled a user to apply lotion to their own back area without having to enlist the assistance of others.

There are many devices and inventions relating to applying lotions and the like to one's back without the aid of another. Such devices include long-handled rollers and other implements. Some devices use strips of material. U.S. Pat. No. 6,607,514, for example, discloses an applicator system for storage and retrieval of applicator strips from a container to be used for applying a liquid preparation to a user's body. An elongated applicator strip is hand held for the user to apply the liquid preparation on remote body parts, such as the back. The applicator strips can be sealed in the container to prevent the evaporation of the liquid preparation contained therein. The applicator strips have laminated layers including an absorbent first layer to receive and retain the liquid preparation. A non-absorbent stabilizing second layer is included to provide strength and dimensional stability. Preferably, the strip includes two outer first layers and one middle second layer. Each elongated applicator strip is preferably about 36 inches in length and about 4.5 inches in width.

Thus, it is desirable to overcome the limitations of the existing applicator systems and to provide an alternative solution.

SUMMARY OF THE INVENTION

The invention resides in a hand-held article for applying lotion to a user, including a user's back or other hard-to-reach places. In broad and general terms, the article includes a housing containing a lotion to be dispensed, and a member, integral to the housing, for transferring the lotion to a user's body. The member may be a roller, in which case the dispenser may be an elongated wand or an existing lotion bottle having threads to which the roller attaches. In some embodiments, the dispenser and the lotion bottle may be removable.

According to an embodiment, the article has an elongated housing with an elongated handle portion, which has an outer surface defining a grip. The elongated housing defines an internal cavity containing a lotion to be dispensed. A roller is supported by the elongated housing and is in communication with the lotion such that the roller delivers the lotion to a user. A spring or pump mechanism pushes the lotion in the internal cavity of the housing such that lotion is delivered to the user through the roller. The elongated housing has a proximal end and an opposing distal end towards the roller. The spring or pump mechanism is disposed at the proximal end for pushing the lotion in the internal cavity. In some embodiments, the spring or pump mechanism has a pump mechanism in an end of the elongated housing.

In some embodiments, the elongated housing has a proximal end and an opposing distal end towards the roller. The spring or pump mechanism is disposed at the distal end for drawing the lotion from the internal cavity towards the roller. In other embodiments, the spring or pump mechanism has a plunger and a spring that pushes the plunger against the lotion in the internal cavity. The elongated housing, elongated handle portion, and roller may be manufactured from the group consisting of glass, metal, plastic, and ceramic. In a non-limiting example, the elongated handle portion is 12-20 inches. The housing may be refillable and may be manufactured from a clear material, which facilitates to ascertain when the housing is full. A band or window of clear plastic may be provided, to indicate the amount of lotion in the housing. Some embodiments may further have a guard piece for protecting the roller. The variety of lotions/liquids may be delivered by the article such as tanning lotion, self-tanning lotions, sun blocks, skin moisturizing creams/oils, body lotions and ointments.

In some embodiments, the elongated housing and the elongated handle portion are configured to allow the elongated housing to pivot with respect to the elongated handle portion. The elongated housing and the elongated handle portion may be configured using a hinge joint or a ball-and-socket joint. This disclosure includes a method of applying a lotion of a user's body. The method includes the steps of providing an article in accordance with the embodiments discussed herein, and delivering lotion to a user's body from the internal cavity through the roller of the article.

BRIEF DESCRIPTION OF THE DRAWINGS

The accompanying drawings, which are included to provide a further understanding of the invention and are incorporated in and constitute a part of this application, illustrate embodiment (s) of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts. In addition, although the terms used in the present invention are selected from generally known and used terms, some of the terms mentioned in the description of the present invention have been selected by the applicant at his or her discretion, the detailed meanings of which are described in relevant parts of the description herein. Furthermore, it is required that the present invention is understood, not simply by the actual terms used but by the meaning of each term lying within.

Figure 1:
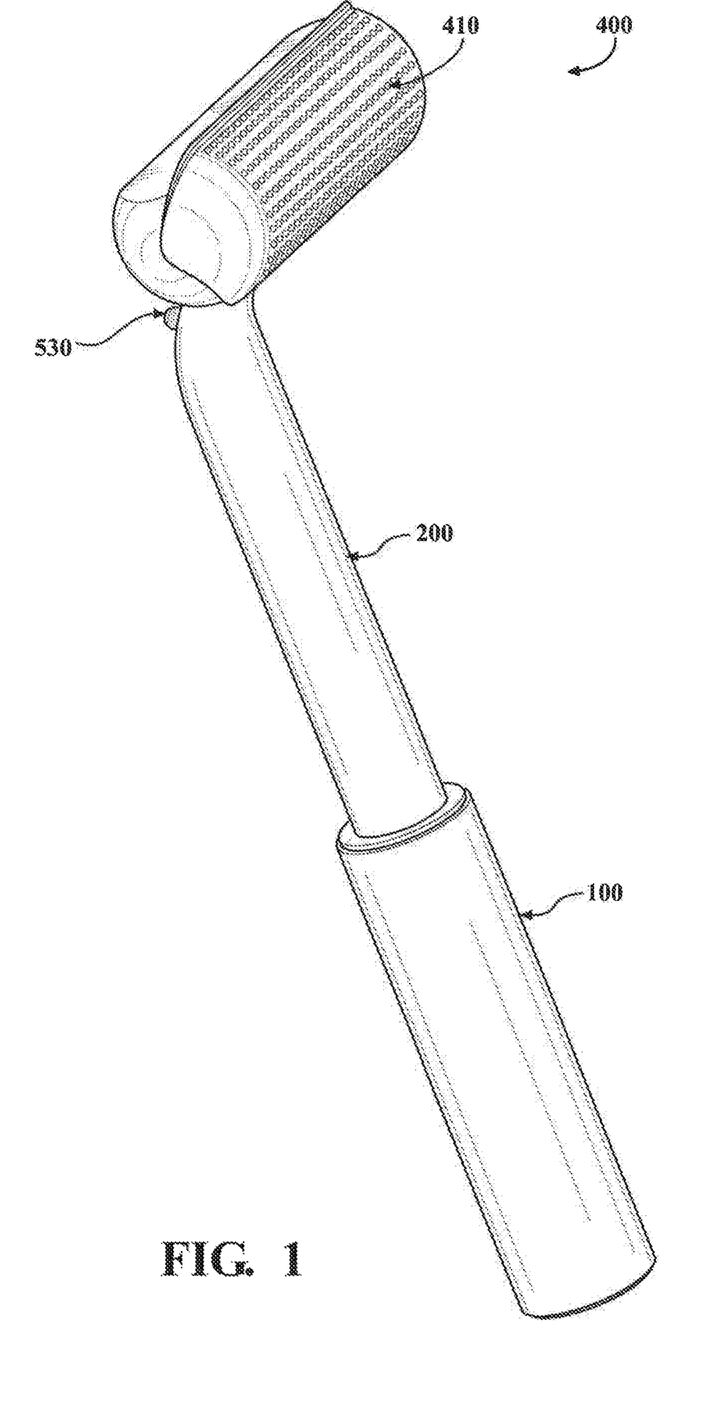
FIG. 1 is a perspective view of an embodiment of the invention.

Embodiments of the present invention provide lotion applicators for different purposes at low cost. FIG. 1 is a perspective view of an article 10 for applying lotion to a user. The article 10 has an elongated housing 200 with an elongated handle portion 100 and a head portion 400. The user grips the article 10 using an outer surface of the elongated handle portion 100 and applies lotion to the user's back or other hard-to-reach places by rubbing the head portion 400 on the back or other hard-to-reach place. The length of the elongated housing 200 is preferably long enough (i.e. 12-20 inches) to enable the user to reach the middle of their back.

Figure 2A:
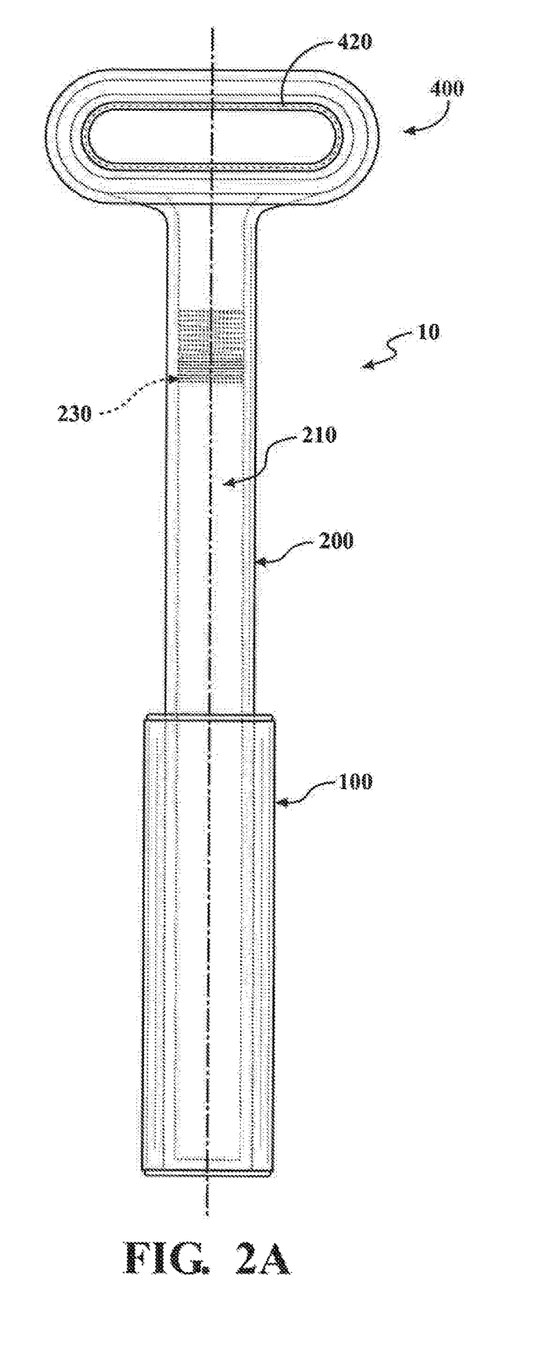
FIG. 2A is a front view of an embodiment of the invention.

FIG. 2A is a front view of an embodiment of the article 10. The article 10 has an elongated housing 200 with an elongated handle portion 100 and a head portion 400. The elongated housing 200 has an internal cavity 210 (shown by broken lines) that contains a lotion or any other liquid to be applied to the body. The article 10 has a spring or pump mechanism 230 for drawing the lotion/liquid from the internal cavity 210 of the elongated housing 200 toward the head portion 400. The head portion 400 has a cylindrical roller 420 that is in fluid communication with the lotion. The user grips the outer surface of the elongated handle portion 100, directs the head portion 400 towards the user's body, and moves the roller 420 on the user's body to deliver the liquid contained in the internal cavity 210.

Figure 2B:
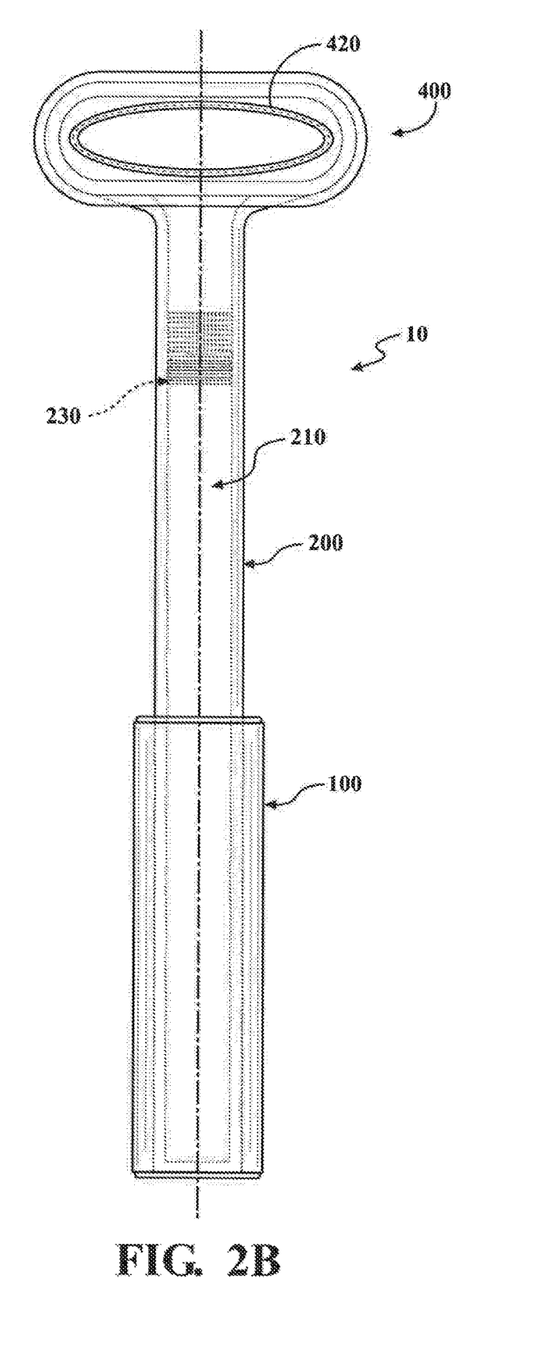
FIG. 2B is a front view of another embodiment of the invention.

FIG. 2B is a side view of another embodiment of the article 10. The article 10 in FIG. 2B is similar to the article 10, but has an oval-shaped roller 420. The oval-shaped roller 420 enhances the user's ability for more skin contact between the shoulder blades. In a non-limiting example, the article 10 according to this disclosure may have a round-shaped, oval-shaped, diamond-shaped, or oblong-shaped roller 420. In some embodiments, the roller is connected to the head portion by snap-on ridges or pins. In some embodiments, the roller is without pin attachments.

Figure 3:
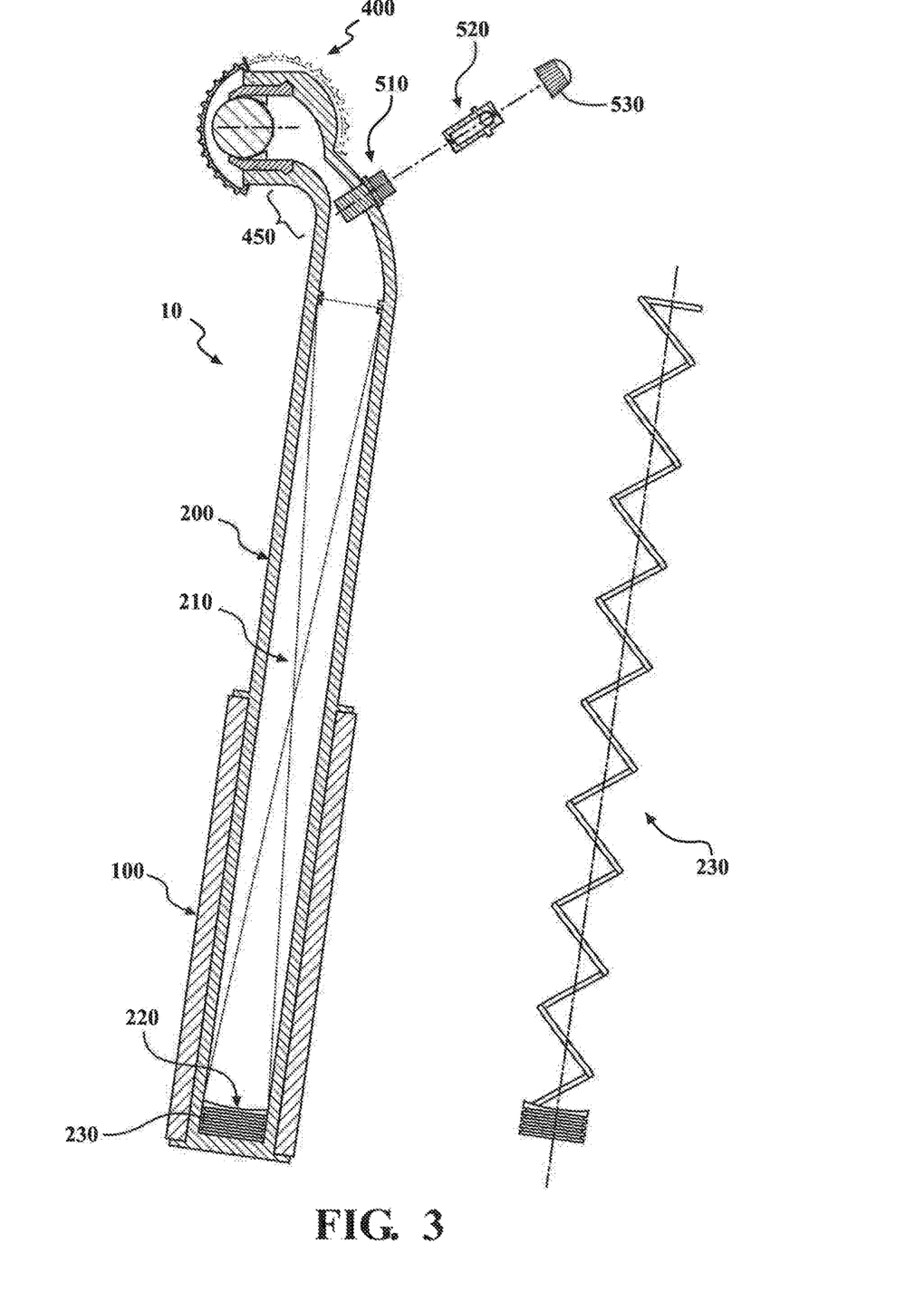
FIG. 3 is a side view of the embodiment shown in FIG. 2A.

FIG. 3 is a side view of an embodiment of the article 10 that may be refilled. The lotion is introduced into the elongated housing via hole 510. The hole 510 has an adapter 520 and the hole may be closed with a cap 530. The cap 530 may be threaded onto the hole 510 or have a snap on/off cover guard. Each elongated housing 200 of the embodiments according to this disclosure has a proximal end and a distal end. A spring or pump mechanism 230 is disposed toward the proximal end inside the internal cavity 210 and the head portion 400 is disposed toward the distal end. The elongated housing 200 has a bent-neck portion 450 disposed toward the distal end that is connected with the head portion 400. In some embodiments, the spring or pump mechanism 230 may have a plunger 220 for drawing the lotion/liquid from the internal cavity 210 of the elongated housing 200 toward the head portion 400. Some embodiments of this disclosure may have a central guide rod for the plunger 220 to travel along.

The spring or pump mechanism 230 may be a compression spring, an extension spring or a manual/powered pump mechanism. FIG. 3 also shows an extension spring along the side of article 10 in its fully extended form. One end of the extension spring is fixedly connected to the elongated housing 200 toward the distal end inside the internal cavity 210. The opposing end of the extension spring is connected with the plunger 220. The plunger 220 moves in the internal cavity 210 from the proximal end towards the distal end for delivering lotion/liquid toward the head portion 400. In some embodiments, the plunger may have a seal to prevent any leakage of the lotion/liquid and/or prevent entry of any contaminants inside the internal cavity. When the article 10 is without any lotion/liquid, the extension spring is coiled together towards the distal end. As the internal cavity 210 is filled with lotion/liquid via the hole 510, the lotion/liquid exerts pressure on the plunger 220 and moves the opposing end of the extension spring toward the proximal end. FIG. 3 shows the extension spring in its fully extended form when the internal cavity is approximately full with the lotion/liquid. In some embodiments, the extension spring arrangement is preferred, and the spring draws the plunger upwardly to maintain the lotion in contact with the roller. This arrangement allows the plunger to be at the proximal end of the chamber, thereby maximizing the capacity. If the spring is below the plunger, the plunger cannot travel completely to the proximal end.

As the user applies lotion/liquid to the body, the opposing end of the spring and the plunger 220 (if used) move from the proximal end of the elongated body 200 toward the distal end for pushing the lotion/liquid in the internal cavity 210 toward the head portion 400. If a compression spring (not shown) is used instead, one end of the compression spring may be fixedly connected to the elongated housing 200 toward the proximal end inside the internal cavity 210. The opposing end of the compression spring is connected with the plunger 220. When the article 10 is without any lotion/liquid, the compression spring is without load and fully extended with the opposing end disposed toward the distal end. As the internal cavity 210 is filled with lotion/liquid via the hole 510, the lotion/liquid exerts pressure on the plunger 220 and moves the opposing end of the compression spring toward the proximal end. A person of skill in the art would be able to use various springs or pump mechanisms for delivering lotion/liquid in the embodiments according to this disclosure.

Figure 4:
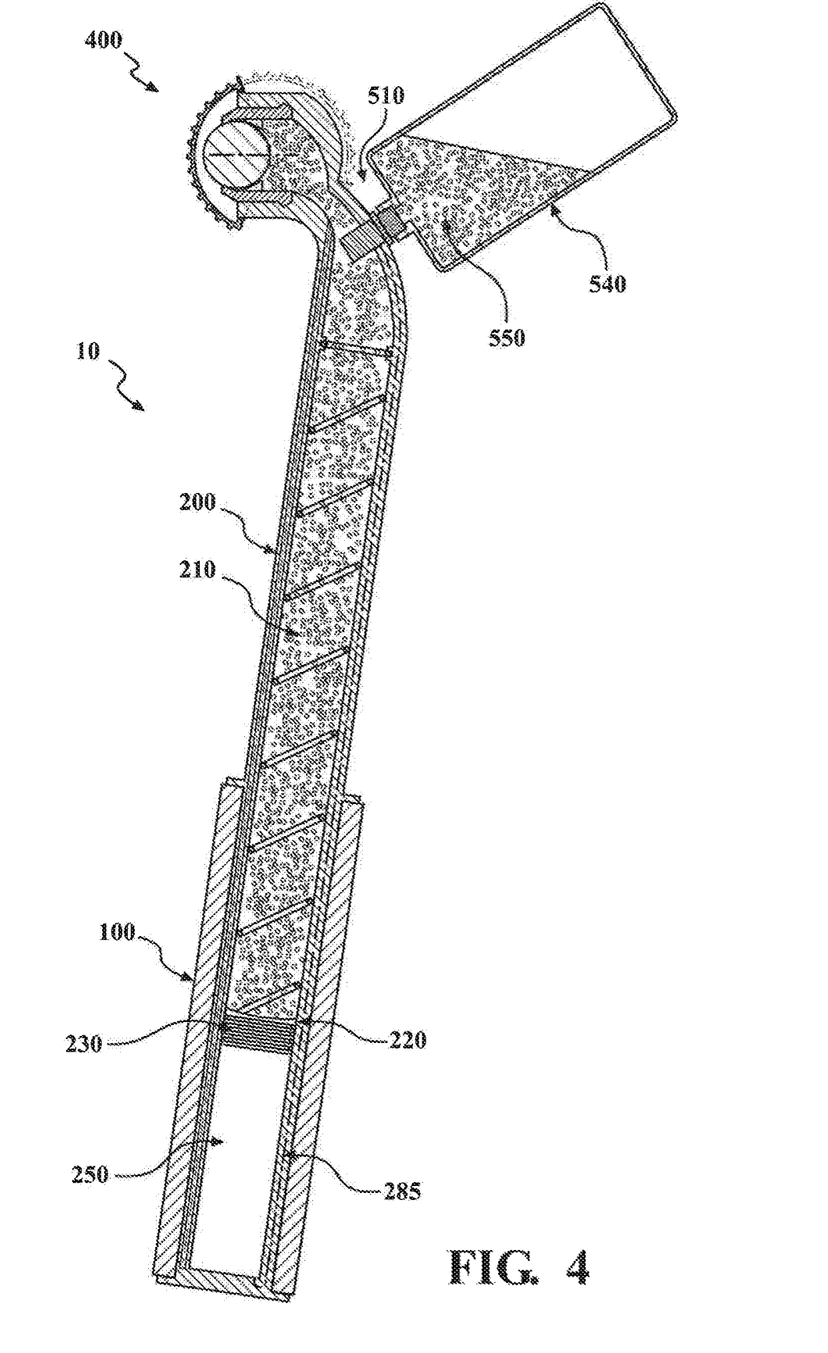
FIG. 4 shows an embodiment of the invention being refilled.

FIG. 4 shows an embodiment of the article 10 being filled/refilled using a refill bottle 540. The refill bottle 540 is connected to the elongated housing 200 via hole 510 to transfer the lotion/liquid 550 to the internal cavity 210. The plunger 220 separates the elongated housing 200 into the internal cavity 210 and the air cavity 250. The space in the elongated housing 200 from the plunger 220 towards the distal end defines the internal cavity 210 and the space in the elongated housing 200 from the plunger 220 towards the proximal end defines the air cavity 250. As the internal cavity 210 is filled with lotion/liquid 550 via the hole 510, the lotion/liquid 550 exerts pressure on the plunger 220 and moves the opposing end of the extension spring toward the proximal end. The article 10 also has an air route 285 to provide an escape route to the air trapped inside the air cavity 250. The air route 285 may introduce air into the air cavity when the plunger 220 moves towards the distal end to prevent creating a vacuum in the air cavity 250. In a non-limiting example, the air route 285 may be a tubular cavity or hole.

Figures 5, 6:
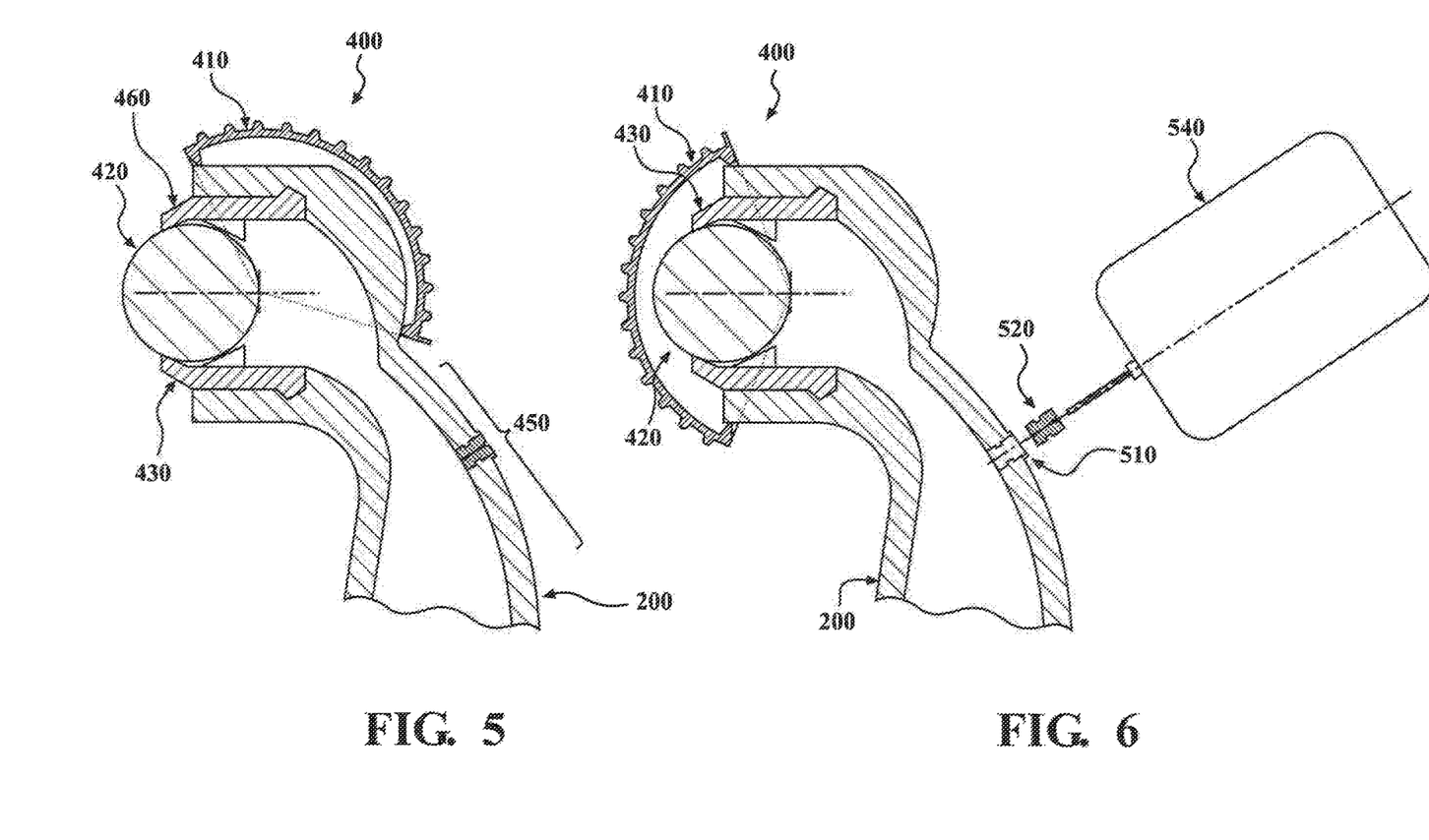
FIG. 5 is a side view of the head portion of an embodiment of the invention.
FIG. 6 is another side view of the head portion of an embodiment of the invention.

FIG. 5 is a side view of a head portion 400 of an article 10 according to this disclosure. A bent-neck portion 450 is disposed toward the distal end of the elongated housing (not shown) and is connected with the head portion 400. The head portion 400 has a roller 420 that is in fluid communication with the lotion. The user directs the head portion 400 towards the user's body, and moves the roller 420 on the user's body to deliver the lotion. In some embodiments, the roller 420 is textured, such as having a light texture that helps draw lotion onto the surface, or dimples or troughs for carrying lotion for application to the user. The head portion 400 has a seal 430 to prevent the lotion from leaking out and acts as a barrier for unwanted entry of contaminants. The seal 430 may comprise deformable elastomeric, rubber or plastic forming suitable material therefor. According to some embodiments, a resilient annular seal is press-fitted with the roller 420 within the head portion 400. The seal 430 has an outer lip 460 that maintains proper contact with the roller 420 to prevent the undesirable leakage of lotion. The outer lip 460 maintains a predetermined pressure on the roller 420. The lotion is delivered to the roller 420 due to the pressure exerted by the plunger 220; the plunger assures that lotion remains in contact with the roller. The lotion is not necessarily pressurized to above atmospheric pressure, though may be in some embodiments, depending on the configuration. Some embodiments have an elastomeric ring in the form of an outer lip which is held in contact with the surface of the roller 420. If the roller is textured, the texture may help move lotion from behind the seal to the exposed portion. The roller may have outwardly or inwardly extending surface features or be otherwise textured for spreading and rubbing the lotion. The roller 420 shown herein represents the roller with the smooth surface as well as the roller with a textured surface.

Some embodiments may have a guard piece 410 to protect the roller when not in use. Such guard piece 410 may be removable or attached and pivotable between retracted and non-retracted position. FIG. 5 shows the guard piece 410 in the retracted position. FIG. 6 is a side view of the head portion 400 of the article 10 shown in FIG. 5. FIG. 6 shows the guard piece 410 in the non-retracted position and is covering the roller 420. The roller 420 is exposed for delivering the lotion 550 to the user in the retracted position and the roller 420 is covered with the guard piece 410 in the non-retracted position. In some embodiments, the surface of the guard piece 410 may be textured or have outwardly extending ridges or nibs for spreading and rubbing the lotion/liquid on the user's body. The guard piece 410 shown herein represents the guard piece with the smooth surface as well as the guard piece with a textured surface/ridges/nibs. The guard piece 410 may be arcuate in cross section. The refillable embodiment of the article 10 is refilled via a hole 510 using a refill bottle 540. An adapter 520 is disposed in the hole 510. The adapter 520 in FIG. 6 is shown outside the hole 510 for clarity. In some embodiments, the adapter 520 is a rubber fitting with a passage for refilling lotion. The refill bottle 540 may have a needle for transferring the lotion/liquid from the refill bottle 540 to the article 10. One-time use or non-refillable embodiments of the article 10 do not have an adapter. The illustrated bottle 540 may also represent part of a filling apparatus, such as a filling machine that fills a disposable version. The needle on the bottle penetrates the adapter for filling and then is withdrawn and the adapter seals the hole.

Figure 7:
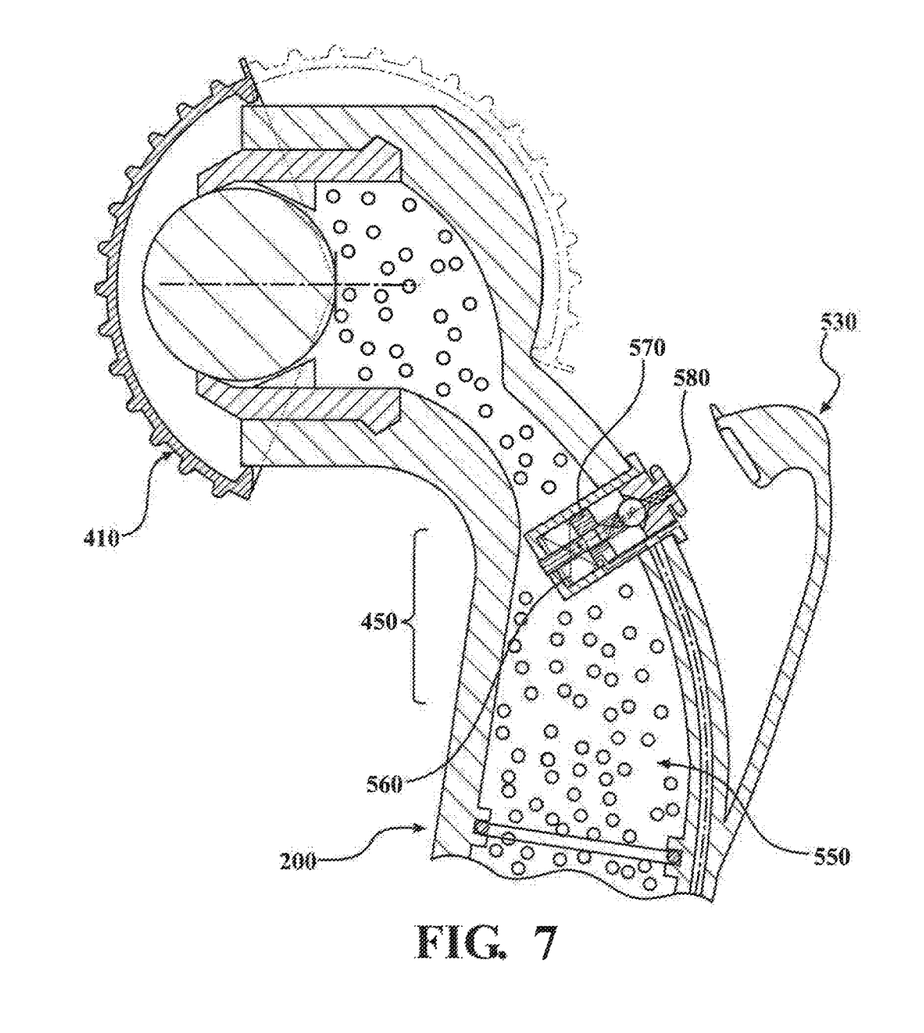
FIG. 7 is yet another side view of the head portion of an embodiment of the invention.

FIG. 7 is a side view of a head portion 400 of an article 10 according to this disclosure. A bent-neck portion 450 is disposed toward the distal end of the elongated housing (not shown) and is connected with the head portion 400. The head portion 400 has a roller 420 that is in fluid communication with the lotion 550. The article 10 is refilled via a hole 510. An adapter is disposed in the hole 510. In a non-limiting example, the adapter has a spring 560, plunger 570, and a screen 580. The hole 510 and the adapter is covered by a snap-on/off cover guard 530. The screen 580 prevents inadvertent entry of solid contaminants during refill. The spring 560 moves the plunger 570 to regulate the flow of lotion 550 and/or the air escaping via air route (discussed above in FIG. 4). The adapter is operable to exhaust air via air route 285 from the air cavity 250 of the elongated housing during refill. In some embodiments, the plunger enables at least part of the air escaping via air route 285 during refill to mix with the incoming lotion/liquid. In other embodiments, the adapter may have an air vent, a check valve mechanism, sealing member and/or is adapted to seal the hole 510 during refill.

Figure 8:
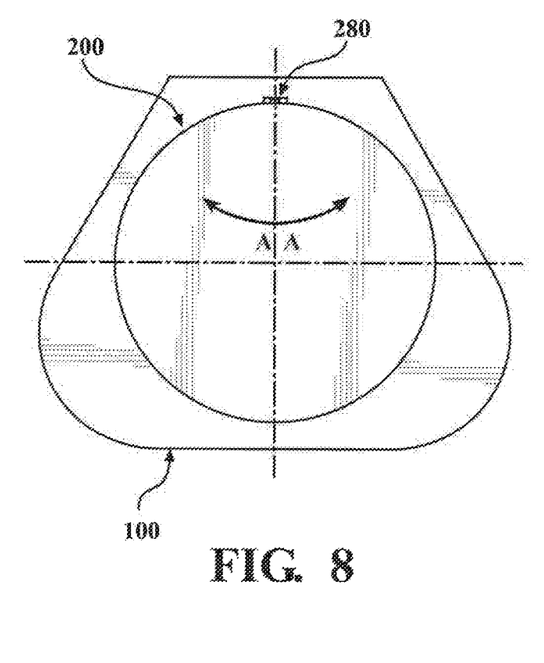
FIG. 8 is a bottom view of the elongated housing of an embodiment of the invention.

FIG. 8 is a bottom view of an elongated housing 200 of an embodiment according to this disclosure. An attaching structure 280 connects the elongated housing 200 with the elongated handle portion 100. In a non-limiting example, the elongated housing 200 is disposed in a cylindrical handle 100 such that the user grips the outer surface of the elongated handle portion 100 and applies lotion to the user's back or other hard-to-reach places by rubbing the head portion on the back or other hard-to-reach place. In some embodiments, the outer surface of the elongated handle portion 100 may be triangular-shaped. The elongated housing 200 and the elongated handle portion 100 are configured to allow the elongated housing 200 to pivot with respect to the elongated handle portion 100. In a non-limiting example, a hinge joint 280 connects the elongated housing 200 with the elongated handle portion 100 and allows for some side-to-side movement within the elongated handle portion 100. In another example, a ball and socket joint 280 provides a pivot joint and allows some rotation to the elongated housing 200 with respect to the elongated handle portion 100.

Figure 9:
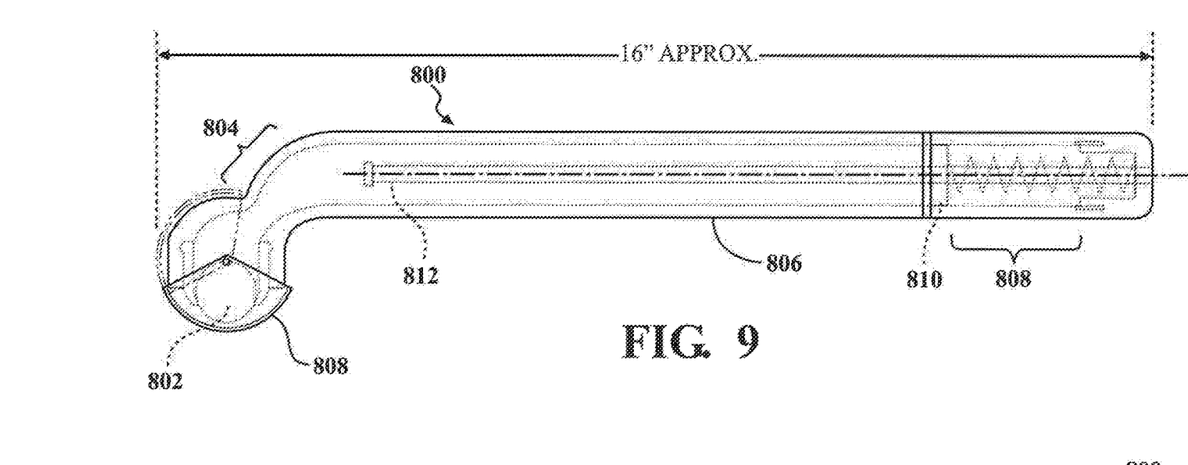
FIG. 9 illustrates an alternative embodiment of the invention.
Figure 10:
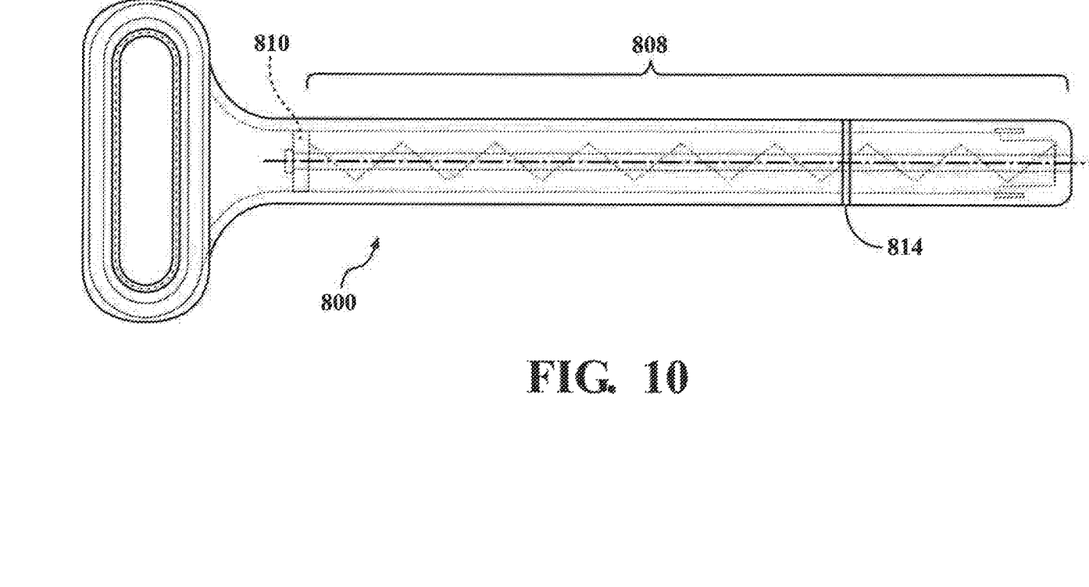
FIG. 10 is a bottom view of the embodiment of FIG. 9.
Figure 11:
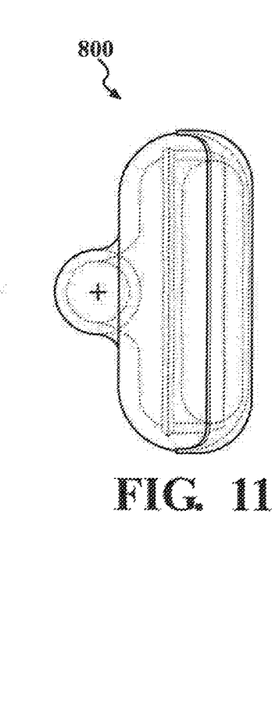
FIG. 11 is a front view of the embodiment of FIG. 9.

FIGS. 9-11 illustrate another embodiment of an article 800, wherein a roller 802 is supported in an elongated housing 806 having a bent neck portion 804. FIG. 9 is a side view of the article 800, FIG. 10 is a bottom view, and FIG. 11 is a front view.

A guard piece 808 may be provided to protect the roller 802 when not in use. Such guard piece may be removable or attached and pivotable between retracted and non-retracted positions. Any desired lotion would be added to the handle, which would be delivered to the body of a user through roller 802. The length of the handle portion would preferably be long enough (i.e., 12-20 inches) to enable a user to reach the middle of their back. The broken lines in FIGS. 9-11 indicate internal structure of some embodiments. For example, the broken lines at 808 may indicate a spring that pushes a plunger 810 against the lotion contained in the housing 806. A central guide rod 812 may be provided for the plunger to travel along. A band or window of clear plastic may be provided, as show at 814, to indicate when the housing is full. A manual pump mechanism may be included in the end of the housing 806 *pf* FIGS. 9-10. The mechanism may include a depressible bulb which operates when the user holds and applies pressure on the depressible bulb.

Various components of the article 10 according to this disclosure (e.g. the elongated housing, roller, guard piece, elongated handle portion etc.) may be manufactured using suitable materials, such as glass, metal, plastic and/or ceramic etc. In some embodiments, the elongated housing 200 is made of a clear or tinted material to indicate if the elongated housing is full. Some embodiments have indicator lines on the elongated housing to show the estimated remaining quantity of the lotion/liquid.

It will be apparent to those skilled in the art that various modifications and variations can be made in the present invention without departing from the spirit or scope of the inventions. Thus, it is intended that the present invention cover the modifications and variations of this invention. The present invention has been described with reference to some embodiments. However, it is realized that variants and equivalents to the preferred embodiments may be provided without departing from the scope of the invention as defined in the accompanying claims. It is to be understood that the detailed description of the present invention are exemplary and explanatory and are intended to provide further explanation of the invention. It is not intended to be exhaustive or to limit embodiments to the precise form disclosed. Changes therein and other uses will occur to those skilled in the art. Such changes and other uses can be made without departing from the scope of the invention as set forth in the following claims.

I claim:

1. A method of applying a lotion to a user's body, comprising:
    providing an applicator comprising:
        an elongated housing having a head portion and an elongated handle portion with an outer surface defining a grip, the elongated housing defining an internal cavity containing a lotion to be dispensed;
        a roller supported by the head portion of the elongated housing and in communication with the internal cavity such that the roller delivers the lotion from the internal cavity to a user;
        the internal cavity being pressurized to deliver the lotion onto the roller;
        a retractable guard piece movably mounted to the head portion of the elongated housing, the retractable guard piece having a convex outer surface with a plurality of surface features, the retractable cover having a non-retracted position wherein the cover covers the roller and a retracted position wherein the roller is exposed;
    moving the retractable guard piece to the retracted position;
    delivering lotion to the user's body from the internal cavity through the roller of the applicator;
    moving the retractable guard piece to the non-retracted position;
    spreading or rubbing the lotion on the user's body using the surface features on the convex outer surface of the retractable guard piece.

2. The method according to claim 1, wherein the applicator further comprises a spring or pump mechanism operable to pressurize the internal cavity, the method further comprising the step of pressurizing the internal cavity using the spring or pump mechanism.

3. The method according to claim 2, wherein the spring or pump mechanism comprises a plunger and a spring that pushes the plunger against the lotion in the internal cavity.

4. The method according to claim 1, wherein the elongated housing, elongated handle portion, and roller are manufactured from the group consisting of glass, metal, plastic, and ceramic.

5. The method according to claim 1, wherein the elongated housing is refillable and has a band or window of clear material to indicate when the housing is full.

6. The method according to claim 1, wherein the lotion is one or more of the following:
    tanning lotion;
    self-tanning lotions;
    sun blocks;
    skin moisturizing creams/oils, and
    body lotions.

7. The method according to claim 1, wherein the elongated housing and the elongated handle portion are configured to allow the elongated housing to pivot with respect to the elongated handle portion.

8. The method according to claim 7, wherein the elongated housing and the elongated handle portion is configured using a hinge joint or a ball-and-socket joint.

9. The method according to claim 1, wherein the applicator further comprises an adapter and an air route, the adapter operable for refilling the internal cavity with the lotion, the adapter operable to exhaust air from the internal cavity via the air route during refilling.

10. The method according to claim 9, wherein the air route is a tubular cavity or hole defined in the elongated housing.

11. The method according to claim 1, wherein the roller is a round-shaped, oval-shaped, diamond-shaped, or oblong-shaped roller.

12. The method according to claim 1, wherein the roller is textured for spreading or rubbing the lotion.

13. The method according to claim 1, wherein the applicator further comprises a seal of resilient material press-fitted with the roller, the seal configured to prevent leakage of the lotion, the seal having outer lips engaging opposing surfaces of the roller.

14. The method according to claim 1, wherein the retractable guard piece movably mounted to the head portion comprises the guard piece being pivotally mounted to the head portion.

15. The method according to claim 1, wherein the retractable guard piece is arcuate in cross section.

16. The method according to claim 1, wherein the plurality of surface features comprise a textured surface or ridges or nibs.

* * * * *